(12) United States Patent
Watson

(10) Patent No.: US 9,056,181 B2
(45) Date of Patent: Jun. 16, 2015

(54) SHUNT VALVE FOR CONTROLLING SIPHON EFFECT

(71) Applicant: David A. Watson, San Jose, CA (US)

(72) Inventor: David A. Watson, San Jose, CA (US)

(*) Notice: Subject to any disclaimer, the term of this patent is extended or adjusted under 35 U.S.C. 154(b) by 139 days.

(21) Appl. No.: 13/765,386

(22) Filed: Feb. 12, 2013

(65) Prior Publication Data

US 2013/0218065 A1 Aug. 22, 2013

Related U.S. Application Data

(60) Provisional application No. 61/598,248, filed on Feb. 13, 2012.

(51) Int. Cl.
*A61M 27/00* (2006.01)
*A61B 17/00* (2006.01)

(52) U.S. Cl.
CPC .............. *A61M 27/006* (2013.01); *A61B 17/00* (2013.01)

(58) Field of Classification Search
CPC . A61M 27/00; A61M 27/002; A61M 27/006; A61M 2027/00; A61M 2027/002; A61M 2027/004; A61F 9/00781
USPC ........................................................ 604/8–10
See application file for complete search history.

(56) References Cited

U.S. PATENT DOCUMENTS

| 4,795,437 | A | * | 1/1989 | Schulte et al. | .................. 604/10 |
| 5,192,265 | A | | 3/1993 | Drake et al. | |
| 6,090,062 | A | | 7/2000 | Sood et al. | |
| 2002/0087111 | A1 | * | 7/2002 | Ethier et al. | ...................... 604/9 |

OTHER PUBLICATIONS

ISA/US, International Search Report and Written Opinion from counterpart International Application PCT/US2013/025900 dated Apr. 19, 2013.

* cited by examiner

*Primary Examiner* — Philip R Wiest
*Assistant Examiner* — Benjamin Klein
(74) *Attorney, Agent, or Firm* — Fuwlider Patton LLP

(57) ABSTRACT

An improved shunt valve for the control of hydrocephalus provides for physiological atmospherically-referenced siphon control that is not adversely affected by overlying tissue. The valve includes one or more porous outer antifouling membranes to protect the flow control membranes from external mechanical tissue pressure, while permitting free movement of the flow control moveable membranes and permitting positive inlet pressure to regulate flow through the improved fluid shunt valve of the invention. The porous membranes are configured to prevent tissue ingrowth into the membranes pores while allowing adequate fluid flow across so as not to inhibit movement of the movable membrane.

17 Claims, 1 Drawing Sheet

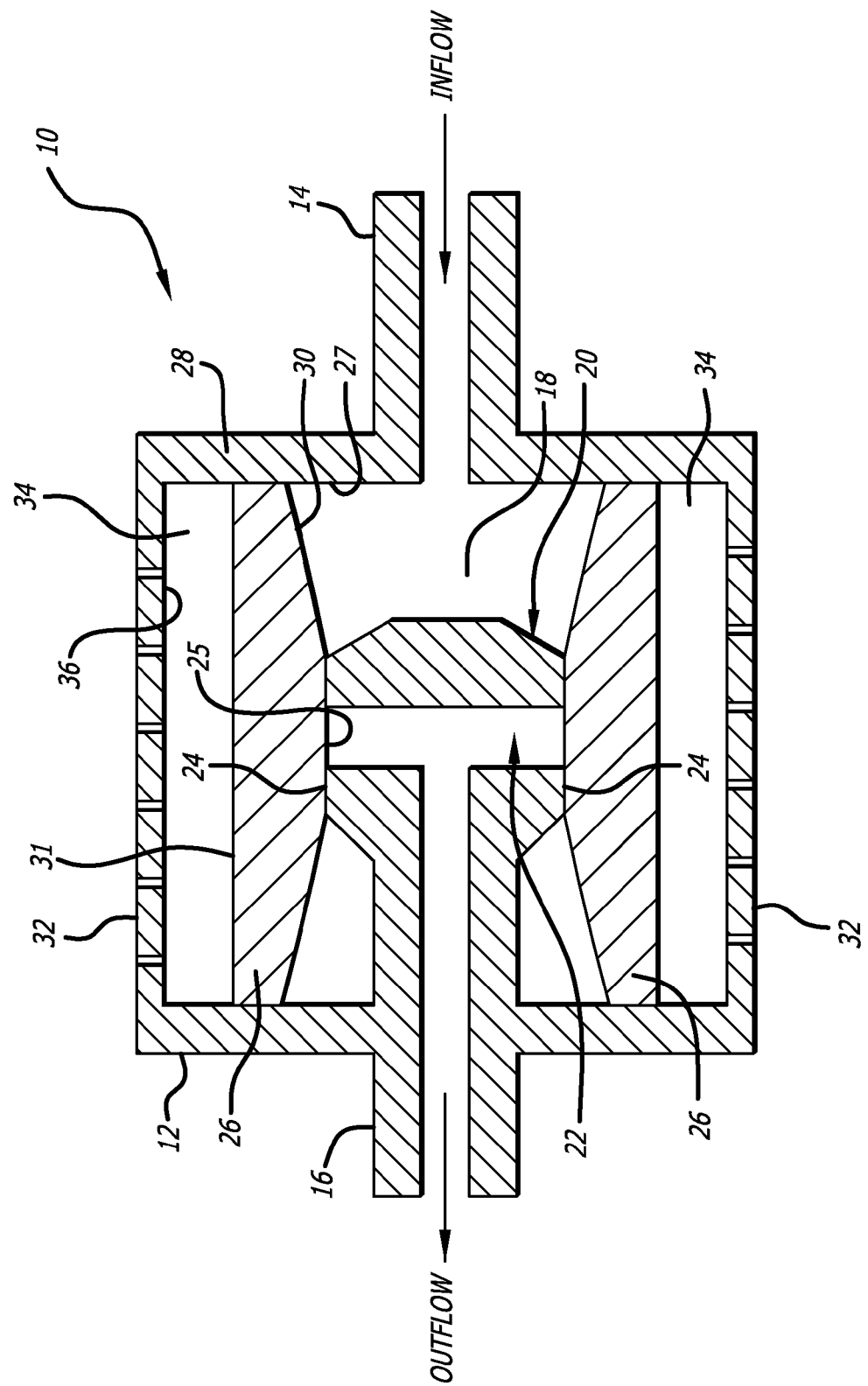

SHUNT VALVE FOR CONTROLLING SIPHON EFFECT

CROSS-REFERENCES TO RELATED APPLICATIONS

This application is based upon and claims priority from Provisional Application No. 61/598,248, filed Feb. 13, 2012, incorporated by reference herein.

BACKGROUND OF THE INVENTION

This invention relates generally to surgically implanted delivery and drainage catheters, such as in shunt systems that drain cerebrospinal fluid from the brain ventricles and pressure sensors implanted in fluid filled spaces or within the parenchyma of tissues. More particularly, this invention relates to an improved shunt valve including outer porous anti-fouling membranes that protect movable siphon control membranes of the shunt from external mechanical pressures. The invention also provides for a means for preventing the mechanical influence of overlying tissue from affecting the accuracy of indwelling pressure sensors.

In order to relieve undesirable accumulation of body fluids it is frequently necessary to provide a shunt for controlled drainage of such fluids from one part of the body to another. Such shunts can be required in the treatment of hydrocephalus, an ailment usually afflicting infants or children in whom fluids which ought to drain away instead accumulate within the brain and thereby exert extreme pressure and skull deforming forces. Accumulated cerebrospinal fluid can be drained away from brain ventricles by a catheter connected to a tube which conducts the fluid away from the brain to be reintroduced into the patient's vasculature. However, excessive fluid flow through such a shunt system can occur due to a siphoning effect of hydrostatic pressure, such as can be created by the elevation of the proximal catheter inlet with respect to the distal catheter outlet such as when a shunted patient is upright. It is also speculated in the hydrocephalus field that 'over drainage' from shunt systems may also be partially caused by abrupt spikes in fluid transport through valves systems caused by physiologic events that transiently increase intra cranial pressure such as sneezing, coughing and REM sleep.

A siphon flow control valve for use in a physiological shunt system is known that limits fluid flow through a shunt system that can otherwise occur due to a siphoning effect of a differential hydrostatic pressure between a catheter inlet and a catheter outlet. The siphon flow control valve includes a molded base that defines a fluid flow pathway between an inlet and an outlet, and that provides an inner wall structure having upper and lower seating surfaces that separate the inlet from the outlet, and a pair of flexible, elastic diaphragms seated against the inner wall structure to control against unwanted flow due to the siphoning effect. However, it has been found that the flexible, elastic diaphragms that are configured on the outer surface of the valve can be forced shut, preventing adequate fluid flow, or can become distorted, allowing excess fluid flow through the siphon control device due to external mechanical tissue pressures.

An adjustable-resistance anti-siphon cerebrospinal fluid shunt is also known that has a substantially rigid housing having an outer gas-filled chamber in pressure communication with a flexible wall of an inner chamber having inlet and outlet ports for fluid flow through the inner chamber, and flow through the inner chamber can be adjusted by controlling pressure in the gas-filled chamber, but since this design is not referenced to changes in atmospheric pressure outside the housing, the fluid flow can be improperly influenced simply by normal changes in atmospheric pressure.

It would be desirable to provide an improved shunt valve for controlling the siphon effect that can occur in shunt systems that; controls the gradient of pressures between the inlet and outlet of the valve, minimizes the influence of the negative hydrostatic pressure, while providing for atmospheric pressure reference, provides for a damping effect to reduce transient spikes in flow rate, and prevents external mechanical tissue pressure from influencing the flow through the valve. The present invention meets these and other needs.

SUMMARY OF THE INVENTION

Briefly and in general terms, the present invention provides for an improved shunt valve for controlling the siphon effect in shunt systems, in which porous outer anti-fouling membranes are provided to prevent external mechanical tissue pressure from adversely influencing the mechanical movement of the underlying movable membranes of the valve, thus permitting free movement of the siphon-effect controlling moveable membranes and permitting a balance between negative outlet pressure and positive inlet pressure to regulate flow through the improved fluid shunt valve of the invention.

The present invention accordingly provides for an improved valve for controlling the siphon effect in shunt systems, for use in surgically implanted systems for draining fluid from one portion of the human body to another, to prevent excessive drainage which may be caused by the siphoning effect of hydrostatic pressure in an outlet catheter. The improved valve of the invention includes a housing containing an outer chamber, an inner chamber disposed within the outer chamber, and a fluid filled space disposed within the outer chamber. The valve also advantageously includes one or more movable, resilient flow control membranes having inner surfaces and outer surfaces, and outer edges attached to the inner surface of the housing wall. The fluid flow path is preferably defined by the inner surfaces of the one or more movable, resilient flow control membranes and the inner surface of the housing wall. An inlet connector is connected to the housing in fluid communication with the inlet port, and an outlet connector is connected to the housing and is in fluid communication with the outlet port, which is defined by an inner wall structure disposed substantially within the fluid flow path and inner surfaces of the one or more movable, resilient flow control membranes. The inner wall structure preferably has a surface defining one or more valve seats against which at least a portion of the one or more movable, resilient flow control membranes are biased to be seated in the presence of downstream negative fluid pressure in the outlet port, to seal against flow from entering the outlet port due to any siphoning effect downstream. When the one or more movable, resilient flow control membranes are seated against the one or more valve seats, the inner surfaces of the one or more movable, resilient flow control membranes separate the outlet port from the inlet port, such that the one or more movable, resilient flow control membranes are acted upon and moves in response to changing pressures in the inlet port, the outlet port and the outer chamber.

At least a portion of the outer surface of the valve contains one or more porous outer anti-fouling membranes, the fluid filled space of the outer chamber is defined by the inner surface of one or more porous outer anti-fouling membranes, the outer surfaces of the one or more movable, resilient flow control membranes and the inner surface of the housing wall. The one or more porous outer anti-fouling membranes are configured to have pores extending therethrough that allow for transfer of fluids while prohibiting tissue ingrowth that would limit long term function of flow across the one or more porous outer anti-fouling membranes.

It is well known in the art of tissue encapsulation, that tissues of the human body cannot penetrate porous membranes with pore sizes generally below 2 to 3 microns in diameter. These membranes can therefor be implanted in tissues for long term applications without tissue infiltration that would otherwise compromise the integrity of the water permeability of the membrane. Therefor, such anti-fouling membranes when properly engineered can provide for adequate volumetric transport of water or saline provided sufficient surface area is provided for the necessary requirement while excluding the ingrowth of tissues into the pores that can inhibit long term viability of the membranes.

In a presently preferred aspect, the one or more movable, resilient flow control membranes are sufficiently flexible to be movable out of sealing engagement with the one or more valve seats in response to positive fluid pressure in the inlet port to allow fluid flow through the valve. In another presently preferred aspect, the one or more movable, resilient flow control membranes are sufficiently flexible to be movable to form at least a partial sealing engagement with the one or more valve seats in response to negative fluid pressure in the outlet port to restrict fluid flow through the shunt valve in response to negative hydrostatic pressure. In a presently preferred aspect, the distance that the resilient membrane must move from the seated position to the unseated condition is a fraction of an inch (in the order of 0.001 inches). Therefor the amount of water that must transport across the anti-fouling membranes into or out of the outer chamber to accommodate normal movement of the underlying resilient flow-control membranes, and thereby preventing hydraulic lock, is nearly zero. In another presently preferred aspect, the resilient movable flow control membranes may be partially inhibited to abrupt and large displacements due to a damping effect caused by the resistance of the transport rate of fluid within the outer chamber across the anti-fouling membranes. Such damping effect may limit extreme sudden transient flow rates by limiting the movements of the resilient flow control membranes by limiting abnormal volumes of the fluid within the outer chamber to transvers the anti-fouling membranes.

In another presently preferred aspect, intracranial fluid pressure within the inlet port acts on at least a portion of the one or more movable, resilient flow control membranes. In another presently preferred aspect, distal fluid pressure within the outlet port (generally created by the non-physiologic hydrostatic pressure within the distal catheter) acts on at least a portion of the one or more movable, resilient flow control membranes defined by an area enclosed within the one or more valve seats. In another presently preferred aspect, the surface area of the one or more movable, resilient flow control membranes that is acted upon by the negative outlet pressure, defined within the one or more valve seats, is substantially smaller than the area that is acted upon by the inlet fluid pressure so as to minimize the total pressure force of the negative hydrostatic pressure acting upon the one or more movable, resilient flow control membranes.

In another presently preferred aspect, the fluid-filled space contains extra-cellular fluids or a gas, or initially contains a gas and through diffusion ultimately contains extra-cellular fluids after implantation.

In another presently preferred aspect, the inner wall structure has a generally cylindrical shape. In another presently preferred aspect, the inner wall structure has one or more seating surfaces defining the one or more valve seats against which at least portions of the one or more movable, resilient flow control membranes are biased to be seated in the presence of downstream fluid pressure in the outlet port, to seal against flow from entering the outlet port from the inlet port due to any siphoning effect downstream through the outlet port. In another presently preferred aspect, the inner wall structure has upper and lower seating surfaces, which preferably are substantially parallel.

In another presently preferred aspect, the one or more porous outer anti-fouling membranes are configured to allow adequate fluid flow across so as not to inhibit movement of the one or more movable, resilient flow control membranes. In another presently preferred aspect, the one or more porous outer anti-fouling membranes are water or saline permeable. In another presently preferred aspect, the one or more porous outer anti-fouling membranes are configured to protect the one or more movable, resilient flow control membranes from direct contact with the body tissues. In another presently preferred aspect, the one or more porous outer anti-fouling membranes are configured to prevent physical contact of the overlying body tissue from the one or more movable, resilient flow control membranes. In another presently preferred aspect, the one or more porous outer anti-fouling membranes are configured to prevent tissue ingrowth into the pores of the one or more porous outer anti-fouling membranes. In another presently preferred aspect, the one or more porous outer anti-fouling membranes are attached to opposing outer end portions of the housing wall. In another presently preferred aspect, the one or more porous outer anti-fouling membranes are spaced apart from the one or more movable, resilient flow control membranes. In another presently preferred aspect, the one or more porous outer anti-fouling membranes are configured to permit free movement of the one or more movable, resilient flow control membranes. In another presently preferred aspect, the one or more porous outer anti-fouling membranes are configured to allow an atmospheric reference pressure to be communicated to the one or more movable, resilient flow control membranes to affect the shunt valve at all times. In another presently preferred aspect, the one or more porous outer anti-fouling membranes are configured to permit the balance between positive fluid inlet pressure and negative outlet pressure acting on the movable resilient membranes to regulate flow through the improved fluid shunt valve. In another presently preferred aspect, the one or more porous outer anti-fouling membranes are configured to prevent hydraulic lock within the outer chamber. In another presently preferred aspect, the one or more porous outer anti-fouling membranes comprises a pair of porous outer anti-fouling membranes. In another presently preferred aspect, the one or more movable, resilient flow control membranes comprises a pair of movable, resilient flow control membranes.

The present invention also provides for an apparatus for preventing an adverse mechanical influence of overlying body tissue on an implantable mechanism having active surfaces. The apparatus includes a porous membrane displaced from and overlying the implantable mechanism, the porous membrane being configured to prevent direct contact of the body tissue with any active surfaces of the implantable mechanism, and a fluid filled space provided between the porous membrane and the implantable mechanism. In a presently preferred aspect, the fluid-filled space contains extra-cellular fluids. In another presently preferred aspect, the fluid-filled space contains extra-cellular fluids or a gas, or initially contains a gas and through diffusion ultimately contains extra-cellular fluids after implantation. In another presently preferred aspect, the porous membrane is configured to prevent tissue ingrowth into pores of the membrane. In another presently preferred aspect, the porous membrane is configured to allow adequate fluid flow across the porous membrane so as not to inhibit function of the implantable mechanism.

These and other features and advantages of the present invention will become more apparent from the following detailed description of the preferred embodiments in conjunction with the accompanying drawing, which illustrates, by way of example, and not limitation, the operation of the invention.

BRIEF DESCRIPTION OF THE DRAWINGS

The FIGURE is a schematic sectional diagram of the improved shunt valve for controlling the siphon effect, according to the present invention.

DETAILED DESCRIPTION OF THE PREFERRED EMBODIMENTS

Referring to the drawings, which are provided by way of example, and not by way of limitation, the present invention provides for a valve such as a shunt valve 10 adapted to be surgically implanted in a tissue space of a body of a mammal for draining fluid from one portion of the body to another for controlling hydrostatic siphon effect, to prevent excessive drainage which may be caused by the siphoning effect of hydrostatic pressure in a distal shunt catheter (not shown).

The valve includes a housing 12, formed to have a shape of a disc when viewed from the top or bottom, for example, although the housing can also be configured to have a cylindrical shape when viewed from the top or bottom. The valve includes an inlet connector 14 configured to be connected to an proximal catheter (not shown) such as surgical tubing or a ventricular catheter, and an outlet connector 16 configured to be connected to a distal catheter (not shown) such as surgical tubing or a peritoneal catheter. The housing can be made of polypropylene or a silicone elastomer, or any other similar suitable material.

The housing defines a fluid flow path comprising an inlet port 18 and an outlet port 22. In one presently preferred aspect, the fluid flow path will contain drainage fluids, or saline (from pre-flushing the valve by the physician prior to implantation), or may initially contain flushing saline, and through physiologic flow through the valve outlet chamber, will ultimately contain the drainage fluids that are meant to be drained from the patient after implantation of the valve.

An inner wall structure 20, typically having a generally cylindrical or tubular shape, is disposed substantially within the fluid flow path in the housing, and defines the outlet port 22 that is in fluid communication with the outlet connector. The inner wall structure typically includes an exterior surface defining at least one valve seat 24 against which at least a portion 25 of at least one movable, resilient flow control membranes 26 is biased to be seated in the presence of downstream negative hydrostatic fluid pressure in the outlet port to form a movable seal against the valve seat(s) to control fluid flow from the inlet port and the outlet port. The pair of movable, resilient flow control membranes preferably are attached at their outer edges to the inner surface 27 of the housing wall 28, and have partial inner surfaces 30 that define an outer surface of the inlet port. The generally remaining inner surface 25 of the movable, resilient flow control membranes along with the valve seat in the housing wall separate the inlet port, from the outlet port.

The movable membranes interact with the valve seat to control fluid flow through the valve in response to any combination of pressures acting on said movable membranes. The movable membranes are referenced to ambient (atmospheric) pressure on their outer surfaces 31. Pressures greater than the reference ambient pressure acting in the inlet port on the inner surface 30 will bias the movable membranes away from the seat to provide for flow though the valve. Negative pressure (as referenced to the ambient pressure) in the outlet port acting on the inner surface 25 of the movable membrane will bias the movable membrane against the valve seat thereby restricting flow. The movable membrane therefore moves in response to the three changing pressures acting upon it. The valve seat is configured such that the area of negative pressure acting on the movable membranes is minimized in comparison to the area acted upon by the pressure in the inlet port so as to minimize the magnitude of inlet pressure necessary to overcome the sealing pressures caused by negative pressure in the outlet port.

The movable membranes are highly effected by any external pressures acting on the outer surfaces of the movable membranes, including ambient pressure and any physical pressure from direct mechanical contact. Although a reference to atmospheric pressure is required for the proper function of the valve, any mechanical pressures or forces acting on the movable membranes can adversely affect the function of the valve. Therefor according to one presently preferred aspect this invention, a means to protect the movable membranes from physical contact while allowing atmospheric ambient pressure is provided.

Porous outer anti-fouling membranes 32 are attached to the housing externally of the movable, resilient flow control membranes to prevent such external mechanical pressures contacting against the movable membranes thereby allowing proper regulated flow through the improved fluid shunt valve due primarily to the gradient of inlet pressure and hydrostatic pressure (as referenced to the ambient pressure acting on the outer surface of the membranes) between the inlet and outlet of the valve. The porous outer anti-fouling membranes are preferably spaced apart from the movable, resilient flow control membranes to define a fluid filled space 34, having an volume defined by the outer surfaces of the movable, resilient flow control membranes and the inner surface of the housing and the inner surfaces 36 of the porous outer anti-fouling membranes. In one presently preferred aspect, the fluid filled space 34 may contain one or more extra-cellular fluids, or a gas, or may initially contain a gas, such as air (as supplied at time of manufacture), and through diffusion across the outer anti-fouling membranes, may ultimately contain extra-cellular fluids after implantation of the valve.

Because the porous outer anti-fouling membranes are also somewhat flexible and movable, they are configured to allow an atmospheric reference pressure to be communicated to the fluid filled space that then references said pressure in the fluid filled space against the outer surfaces of the pair of movable, resilient flow control membranes to provide reference atmospheric pressure to the shunt valve at all times. Since the porous outer anti-fouling membranes, are permeable to fluid flow though the pores, hydraulic lock within the fluid filled space is avoided if the porous outer anti-fouling membranes are being mechanically constrained by overlying tissue, which is unavoidable when the valve is implanted within tissue spaces of mammals.

When the housing has a tubular configuration, a single tubular porous outer anti-fouling membrane may be provided displaced around the outside of the housing having a substantially tubular shape and encasing a single substantially tubular movable membrane and defining the fluid filled space there between. The inner surface of the tubular movable membrane in conjunction with a generally radially configured inner wall with one or more valve seats define the fluid flow path from the inlet port to the outlet port through one or more valve seats provided by the inner wall structure.

It is also envisioned that the porous membranes that are configured to facilitate and protect the movement of underlying membranes could also be used to protect the delicate surfaces of implantable mechanisms such as implantable pressure sensors.

It will be apparent from the foregoing that while particular forms of the invention have been illustrated and described, various modifications can be made without departing from the spirit and scope of the invention.

What is claimed is:

1. A surgically implantable valve for draining fluid from one portion of the body to another for controlling hydrostatic siphon effect, said valve comprising:
    a housing containing an outer chamber, an inner chamber disposed within said outer chamber, at least one movable, resilient flow control membrane defining at least a portion of a boundary between said inner chamber and said outer chamber, said inner chamber including an inlet port, and at least one tubular dividing wall disposed within said at least one movable, resilient flow control membrane, said at least one tubular dividing wall defining an outlet port within said at least one tubular dividing wall, and said at least one tubular dividing wall defining at least one valve seat adjacent to said at least one movable, resilient flow control membrane separating said inlet port from said outlet port;
    wherein the at least one movable, resilient flow control membrane has an inner surface and an outer surface, said outer surface is at least partially in fluid communication with said outer chamber, said inner surface of said at least one movable, resilient flow control membrane is at least partially in fluid communication with said outlet chamber and at least partially in fluid communication with the inlet chamber, said at least one movable, resilient flow control membrane is acted upon and moves in response to changing pressures in said inlet port, said outlet port and said outer chamber, and said at least one movable, resilient flow control membrane is configured to at least partially seal against said at least one valve seat to restrict flow through said at least one valve seat in response to the changing pressures; and
    wherein at least one porous anti-fouling membrane is attached to the housing externally of said at least one movable, resilient flow control membrane, said at least one porous anti-fouling membrane having pores extending therethrough configured to allow for transfer of fluids across said at least one porous anti-fouling membrane into said outer chamber.

2. The valve of claim 1, wherein said at least one movable, resilient flow control membrane is sufficiently flexible to be movable out of sealing engagement with said at least one valve seat in response to positive fluid pressure in the inlet port to allow fluid flow through the valve.

3. The valve of claim 1, wherein said at least one movable, resilient flow control membrane is sufficiently flexible to be movable to form at least a partial sealing engagement with said at least one valve seat in response to negative fluid pressure in the outlet port to restrict fluid flow through the shunt valve in response to negative hydrostatic pressure.

4. The valve of claim 1, wherein fluid pressure within said inlet port acts on at least a portion of said at least one movable, resilient flow control membrane.

5. The valve of claim 1, wherein fluid pressure within the outlet port acts on at least a portion of said at least one movable, resilient flow control membrane defined by an area enclosed within said at least one valve seat.

6. The valve of claim 5, wherein the surface area defined within said at least one valve seat is substantially smaller than an area of said at least one movable, resilient flow control membrane that is acted upon by the inlet fluid pressure so as to minimize a total pressure force of a negative pressure acting upon said at least one movable, resilient flow control membrane.

7. The valve of claim 1, wherein said outer chamber comprises a fluid-filled space that contains extra-cellular fluids.

8. The valve of claim 7, wherein said fluid-filled space contains a gas.

9. The valve of claim 7, wherein said fluid-filled space initially contains a gas and through diffusion ultimately contains extra-cellular fluids after implantation.

10. The valve of claim 1, wherein said at least one porous anti-fouling membrane comprises a generally tubular outer anti-fouling membrane.

11. The valve of claim 1, wherein said at least one porous anti-fouling membrane comprises generally flat anti-fouling membranes.

12. The valve of claim 1, wherein said at least one porous anti-fouling membrane is configured to allow adequate fluid flow across so as not to adversely inhibit movement of said at least one movable, resilient flow control membrane.

13. The valve of claim 1, wherein said at least one porous anti-fouling membrane is configured to protect said at least one movable, resilient flow control membrane from direct contact with the body tissues.

14. The valve of claim 1, wherein said at least one porous anti-fouling membrane is configured to prevent tissue ingrowth into the pores of said at least one porous anti-fouling membrane.

15. The valve of claim 1, wherein said at least one porous anti-fouling membrane is spaced apart from said at least one movable, resilient flow control membrane.

16. The valve of claim 1, wherein said at least one porous anti-fouling membrane is configured to allow an atmospheric reference pressure to be communicated to said at least one outer chamber.

17. The valve of claim 1, wherein said at least one porous anti-fouling membrane is configured to prevent hydraulic lock within the outer chamber.

* * * * *